US008668705B2

(12) United States Patent
Johnston et al.

(10) Patent No.: US 8,668,705 B2

(45) Date of Patent: Mar. 11, 2014

(54) LATCHING ANCHOR DEVICE

(75) Inventors: Andrew Johnston, Redwood City, CA (US); Micahel Wei, Redwood City, CA (US); Theodore C. Lamson, Pleasanton, CA (US); Matthew McLean, San Francisco, CA (US); Joseph Catanese, III, San Leandro, CA (US); Floria Cheng, San Francisco, CA (US); Ryan R. Braymer, Clifton Park, NY (US); Eric J. Claude, Vienna, VA (US); Christian L. Haller, Alexandria, VA (US); Ralph S. Paul, Alexandria, VA (US); Ashley K. Wallin, Marietta, GA (US)

(73) Assignee: NeoTract, Inc., Pleasanton, CA (US)

( * ) Notice: Subject to any disclaimer, the term of this patent is extended or adjusted under 35 U.S.C. 154(b) by 546 days.

(21) Appl. No.: 12/852,939

(22) Filed: Aug. 9, 2010

(65) Prior Publication Data

US 2011/0046648 A1 Feb. 24, 2011

Related U.S. Application Data

(63) Continuation-in-part of application No. 12/852,243, filed on Aug. 6, 2010, now Pat. No. 8,333,776, and a continuation-in-part of application No. 12/512,674, filed on Jul. 30, 2009, now Pat. No. 8,216,254, application No. 12/852,939, which is a continuation-in-part of application No. 11/775,162, filed on Jul. 9, 2007, and a continuation-in-part of application No. 11/671,914, filed on Feb. 6, 2007, now Pat. No. 8,157,815, and a continuation-in-part of application No. 11/492,690, filed on Jul. 24, 2006, now Pat. No. 7,896,891, and a continuation-in-part of application No. 11/833,660, filed on Aug. 3, 2007, which is a continuation of application No. 11/318,246, filed on Dec. 22, 2005, now Pat. No. 7,645,286, application No. 12/852,939, which is a continuation-in-part of application No. 11/838,036, filed on Aug. 13, 2007, now Pat. No. 7,914,542, which is a continuation of application No. 11/134,870, filed on May 20, 2005, now Pat. No. 7,758,594.

(60) Provisional application No. 61/084,937, filed on Jul. 30, 2008.

(51) Int. Cl.
*A61B 17/08* (2006.01)

(52) U.S. Cl.
USPC .......... 606/151

(58) Field of Classification Search
USPC ......... 606/139, 144–146, 148–151, 153, 157, 606/232
See application file for complete search history.

(56) References Cited

U.S. PATENT DOCUMENTS 659,422 A 10/1900 Shidler
780,392 A 1/1905 Wanamaker et al.

(Continued)

FOREIGN PATENT DOCUMENTS

DE 10159470 6/2003
EP 0246836 12/1991

(Continued)

OTHER PUBLICATIONS

Sharp, Howard T., M.D., et al., “Instruments and Methods—The 4-S Modification of the Roeder Knot: How to Tie It”, Obstetrics & Gynecology, p. 1004-1006, vol. 90, No. 6, Dec. 1997.

(Continued)

*Primary Examiner* — Gregory Anderson

(74) *Attorney, Agent, or Firm* — Steptoe & Johnson LLP

(57) ABSTRACT

An anchor that secures to a connector as part of an anchor assembly is disclosed. The proximal anchor includes a pair of spaced apart prongs which join together at a slot inception. The prongs are shaped and sized of a configuration to define a catch or latching structure. The prongs are configured to capture and deform the suture between the protrusions and prevent the suture from disengaging from the slotted anchor device once engaged.

8 Claims, 10 Drawing Sheets

96 97 98 96 84

(56) References Cited

U.S. PATENT DOCUMENTS 789,467 A 5/1905 West
2,579,192 A 12/1951 Kohl
2,646,298 A 7/1953 Leary
2,697,624 A 12/1954 Thomas
2,734,299 A 2/1956 Masson
2,825,592 A 3/1958 Semple
3,326,586 A 6/1967 Frost et al.
3,470,834 A 10/1969 Bone
3,521,918 A 7/1970 Hammond
3,541,591 A * 11/1970 Hoegerman .................. 606/232
3,713,680 A 1/1973 Pagano
3,716,058 A 2/1973 Tanner, Jr.
3,756,638 A 9/1973 Stockberger
3,873,140 A 3/1975 Bloch
3,875,648 A 4/1975 Bone
3,931,667 A 1/1976 Merser et al.
3,976,079 A 8/1976 Samuels et al.
4,006,747 A 2/1977 Kronenthal et al.
4,210,148 A 7/1980 Stivala
4,235,238 A 11/1980 Ogiu et al.
4,291,698 A 9/1981 Fuchs et al.
4,409,974 A 10/1983 Freedland
4,493,323 A 1/1985 Albright et al.
4,513,746 A 4/1985 Aranyi
4,621,640 A 11/1986 Mulhollan et al.
4,657,461 A 4/1987 Smith
4,669,473 A 6/1987 Richards et al.
4,705,040 A 11/1987 Mueller et al.
4,714,281 A 12/1987 Peck
4,738,255 A 4/1988 Goble et al.
4,741,330 A 5/1988 Hayhurst
4,744,364 A 5/1988 Kensey
4,750,492 A 6/1988 Jacobs
4,762,128 A 8/1988 Rosenbluth
4,823,794 A 4/1989 Pierce
4,899,743 A 2/1990 Nicholson et al.
4,926,860 A 5/1990 Stice et al.
4,946,468 A 8/1990 Li
4,955,913 A 9/1990 Robinson
4,968,315 A 11/1990 Gatturna et al.
5,002,550 A 3/1991 Li
5,041,129 A 8/1991 Hayhurst et al.
5,046,513 A 9/1991 Gatturna et al.
5,053,046 A 10/1991 Janese
5,078,731 A * 1/1992 Hayhurst ...................... 606/232
5,100,421 A 3/1992 Christoudias
5,123,914 A 6/1992 Cope
5,129,912 A 7/1992 Noda et al.
5,160,339 A * 11/1992 Chen et al. .................... 606/158
5,192,303 A 3/1993 Gatturna et al.
5,203,787 A 4/1993 Noblitt et al.
5,217,470 A 6/1993 Weston
5,217,486 A 6/1993 Rice et al.
5,234,454 A 8/1993 Bangs
5,236,445 A 8/1993 Hayhurst et al.
5,258,015 A 11/1993 Li et al.
5,269,809 A 12/1993 Hayhurst et al.
5,330,488 A 7/1994 Goldrath
5,334,200 A 8/1994 Johnson
5,336,240 A 8/1994 Metzler et al.
5,354,271 A 10/1994 Voda
5,358,511 A 10/1994 Gatturna et al.
5,364,408 A 11/1994 Gordon
5,366,490 A 11/1994 Edwards et al.
5,368,599 A 11/1994 Hirsch et al.
5,370,646 A 12/1994 Reese et al.
5,380,334 A 1/1995 Torrie et al.
5,391,182 A 2/1995 Chin
5,403,348 A 4/1995 Bonutti
5,405,352 A 4/1995 Weston
5,411,520 A 5/1995 Nash et al.
5,417,691 A 5/1995 Hayhurst
5,435,805 A 7/1995 Edwards et al.
5,470,337 A 11/1995 Moss
5,472,446 A 12/1995 De la Torre
5,480,406 A 1/1996 Nolan et al.
5,501,690 A 3/1996 Measamer et al.
5,507,754 A 4/1996 Green et al.
5,522,846 A 6/1996 Bonutti
5,531,763 A 7/1996 Mastri et al.
5,536,240 A 7/1996 Edwards et al.
5,540,704 A 7/1996 Gordon et al.
5,545,171 A 8/1996 Sharkey et al.
5,545,178 A 8/1996 Kensey et al.
5,550,172 A 8/1996 Regula et al.
5,554,162 A 9/1996 DeLange
5,554,171 A 9/1996 Gatturna et al.
5,562,689 A 10/1996 Green et al.
5,569,305 A 10/1996 Bonutti
5,571,104 A 11/1996 Li
5,573,540 A 11/1996 Yoon
5,578,044 A 11/1996 Gordon et al.
5,591,177 A 1/1997 Lehrer
5,593,421 A 1/1997 Bauer
5,611,515 A 3/1997 Benderev et al.
5,626,614 A 5/1997 Hart
5,630,824 A 5/1997 Hart
5,647,836 A 7/1997 Blake, III et al.
5,665,109 A 9/1997 Yoon
5,667,486 A 9/1997 Mikulich et al.
5,669,917 A 9/1997 Sauer et al.
5,690,649 A 11/1997 Li
5,690,677 A 11/1997 Schmiedling et al.
5,697,950 A 12/1997 Fucci et al.
5,707,394 A 1/1998 Miller et al.
5,716,368 A 2/1998 De la Torre
5,718,717 A 2/1998 Bonutti
5,725,556 A 3/1998 Moser et al.
5,725,557 A 3/1998 Gatturna et al.
5,733,306 A 3/1998 Bonutti
5,741,276 A 4/1998 Poloyko et al.
5,746,753 A 5/1998 Sullivan et al.
5,749,846 A 5/1998 Edwards et al.
5,752,963 A 5/1998 Allard et al.
5,782,862 A 7/1998 Bonutti
5,782,864 A 7/1998 Lizardi
5,800,445 A 9/1998 Ratcliff et al.
5,807,403 A 9/1998 Beyer et al.
5,810,848 A 9/1998 Hayhurst
5,810,853 A * 9/1998 Yoon ............................ 606/151
5,814,072 A 9/1998 Bonutti
5,830,221 A 11/1998 Stein
5,845,645 A 12/1998 Bonutti
5,846,254 A 12/1998 Schulze et al.
5,861,002 A 1/1999 Desai
5,868,762 A 2/1999 Cragg et al.
5,873,891 A 2/1999 Sohn
5,897,574 A 4/1999 Bonutti
5,899,911 A 5/1999 Carter
5,899,921 A 5/1999 Caspari et al.
5,904,696 A 5/1999 Rosenman
5,908,428 A 6/1999 Scirica et al.
5,919,198 A 7/1999 Graves, Jr. et al.
5,919,202 A 7/1999 Yoon
5,921,986 A 7/1999 Bonutti
5,928,252 A 7/1999 Steadman et al.
5,931,844 A 8/1999 Thompson et al.
5,944,739 A 8/1999 Zlock et al.
5,948,001 A 9/1999 Larsen
5,948,002 A 9/1999 Bonutti
5,954,057 A 9/1999 Li
5,954,747 A 9/1999 Clark
5,964,732 A 10/1999 Wilard
5,971,447 A 10/1999 Steck, III
6,010,514 A 1/2000 Burney et al.
6,011,525 A 1/2000 Piole
6,030,393 A 2/2000 Corlew
6,033,430 A 3/2000 Bonutti
6,036,701 A 3/2000 Rosenman
6,048,351 A 4/2000 Gordon et al.
6,053,908 A 4/2000 Crainich et al.
6,056,722 A 5/2000 Jayaraman
6,056,772 A 5/2000 Bonutti
6,068,648 A 5/2000 Cole et al.

(56) References Cited

U.S. PATENT DOCUMENTS 6,080,167 A 6/2000 Lyell
6,086,608 A 7/2000 Ek et al.
6,110,183 A 8/2000 Cope
6,117,160 A 9/2000 Bonutti
6,117,161 A 9/2000 Li et al.
6,120,539 A 9/2000 Eldridge et al.
6,139,555 A 10/2000 Hart et al.
RE36,974 E 11/2000 Bonutti
6,143,006 A 11/2000 Chan
6,159,234 A 12/2000 Bonutti et al.
6,200,329 B1 3/2001 Fung et al.
6,206,895 B1 3/2001 Levinson
6,228,096 B1 5/2001 Marchand
6,258,124 B1 7/2001 Darois et al.
6,261,302 B1 7/2001 Voegele et al.
6,270,530 B1 8/2001 Eldridge et al.
6,280,460 B1 8/2001 Bolduc et al.
6,290,711 B1 9/2001 Caspari et al.
6,312,448 B1 11/2001 Bonutti
6,319,263 B1 11/2001 Levinson
6,322,112 B1 11/2001 Duncan
6,332,889 B1 12/2001 Sancoff et al.
6,398,795 B1 6/2002 McAllister et al.
6,425,900 B1 7/2002 Knodel et al.
6,428,562 B2 8/2002 Bonutti
6,436,107 B1 8/2002 Wang et al.
6,461,355 B2 10/2002 Svejkovsky et al.
6,482,235 B1 11/2002 Lambrecht et al.
6,488,691 B1 12/2002 Carroll et al.
6,491,707 B2 12/2002 Makower et al.
6,494,888 B1 12/2002 Laufer et al.
6,500,195 B2 12/2002 Bonutti
6,506,190 B1 1/2003 Walshe
6,506,196 B1 1/2003 Laufer
6,517,569 B2 2/2003 Mikus et al.
6,527,702 B2 3/2003 Whalen et al.
6,527,794 B1 3/2003 McDevitt et al.
6,530,932 B1 3/2003 Swayze et al.
6,533,796 B1 3/2003 Sauer et al.
6,547,725 B1 4/2003 Paolitto et al.
6,551,328 B2 4/2003 Kortenbach
6,551,333 B2 4/2003 Kuhns et al.
6,565,578 B1 5/2003 Peifer et al.
6,569,187 B1 5/2003 Bonutti et al.
6,572,626 B1 6/2003 Knodel et al.
6,572,635 B1 6/2003 Bonutti
6,572,653 B1 6/2003 Simonson
6,592,609 B1 7/2003 Bonutti
6,596,013 B2 7/2003 Yang et al.
6,599,311 B1 7/2003 Biggs et al.
6,626,913 B1 9/2003 McKinnon et al.
6,626,916 B1 9/2003 Yeung et al.
6,626,919 B1 9/2003 Swanstrom
6,629,534 B1 10/2003 Dell et al.
6,641,592 B1 11/2003 Sauer et al.
6,656,182 B1 12/2003 Hayhurst
6,660,023 B2 12/2003 McDevitt et al.
6,663,589 B1 12/2003 Halevy
6,663,639 B1 12/2003 Laufer et al.
6,699,263 B2 3/2004 Cope
6,706,047 B2 3/2004 Trout et al.
6,709,493 B2 3/2004 DeGuiseppi et al.
6,715,804 B2 4/2004 Beers
6,719,709 B2 4/2004 Whalen et al.
6,730,112 B2 5/2004 Levinson
6,736,823 B2 5/2004 Darois et al.
6,736,854 B2 5/2004 Vadurro et al.
6,740,098 B2 5/2004 Abrams et al.
6,767,037 B2 7/2004 Wenstrom, Jr.
6,770,076 B2 8/2004 Foerster
6,773,438 B1 8/2004 Knodel et al.
6,773,441 B1 8/2004 Laufer et al.
6,790,213 B2 9/2004 Cherok et al.
6,802,846 B2 10/2004 Hauschild et al.
6,821,282 B2 11/2004 Perry et al.
6,821,285 B2 11/2004 Laufer et al.
6,821,291 B2 11/2004 Bolea et al.
6,835,200 B2 12/2004 Laufer et al.
6,905,475 B2 6/2005 Hauschild et al.
6,908,473 B2 6/2005 Skiba et al.
6,926,732 B2 8/2005 Derus et al.
6,951,565 B2 10/2005 Keane et al.
6,986,775 B2 1/2006 Morales et al.
6,991,596 B2 1/2006 Whalen et al.
6,991,647 B2 1/2006 Jadhav
6,997,940 B2 2/2006 Bonutti
7,001,327 B2 2/2006 Whalen et al.
7,011,688 B2 3/2006 Gryska et al.
7,015,253 B2 3/2006 Escandon et al.
7,048,698 B2 5/2006 Whalen et al.
7,048,747 B2 5/2006 Arcia et al.
7,060,077 B2 6/2006 Gordon et al.
7,081,126 B2 7/2006 McDevitt et al.
7,083,638 B2 8/2006 Foerster
7,087,073 B2 8/2006 Bonutti
7,089,064 B2 8/2006 Manker et al.
7,090,690 B2 8/2006 Foerster et al.
7,093,601 B2 8/2006 Manker et al.
7,105,004 B2 9/2006 Dicesare et al.
7,108,655 B2 9/2006 Whalen et al.
7,141,038 B2 11/2006 Whalen et al.
7,153,314 B2 12/2006 Laufer et al.
7,179,225 B2 2/2007 Shluzas
7,226,558 B2 6/2007 Nieman et al.
7,232,448 B2 6/2007 Battles et al.
7,288,063 B2 10/2007 Petros et al.
7,303,108 B2 12/2007 Shelton, IV
7,320,701 B2 1/2008 Haut et al.
7,322,974 B2 1/2008 Swoyer et al.
7,334,822 B1 2/2008 Hines et al.
7,340,300 B2 3/2008 Christopherson et al.
7,399,304 B2 7/2008 Gambale et al.
7,402,166 B2 7/2008 Feigl
7,416,554 B2 8/2008 Lam et al.
7,553,317 B2 6/2009 Wesenburgh, II et al.
7,608,108 B2 10/2009 Bhatnagar et al.
7,658,311 B2 2/2010 Boudreaux
7,674,275 B2 3/2010 Martin et al.
7,727,248 B2 6/2010 Smith et al.
2001/0044639 A1 11/2001 Levinson
2002/0095154 A1 7/2002 Atkinson et al.
2002/0128684 A1 9/2002 Foerster
2002/0161382 A1 10/2002 Neisz et al.
2002/0193809 A1 12/2002 Meade
2003/0109769 A1 6/2003 Lowery et al.
2003/0191497 A1 10/2003 Cope
2003/0204195 A1 10/2003 Keane et al.
2004/0030217 A1 2/2004 Yeung et al.
2004/0043052 A1 3/2004 Hunter et al.
2004/0078046 A1 4/2004 Barzell et al.
2004/0193191 A1 9/2004 Starksen et al.
2004/0193194 A1 9/2004 Laufer et al.
2004/0194790 A1 10/2004 Laufer et al.
2004/0243178 A1 12/2004 Haut et al.
2004/0243179 A1 12/2004 Foerster
2004/0243180 A1 12/2004 Donnelly
2004/0243227 A1 12/2004 Starksen et al.
2004/0260345 A1 12/2004 Foerster
2005/0055087 A1 3/2005 Starksen
2005/0065550 A1 3/2005 Starksen et al.
2005/0107811 A1 5/2005 Starksen et al.
2005/0107812 A1 5/2005 Starksen et al.
2005/0154401 A1 7/2005 Weldon et al.
2005/0177181 A1 8/2005 Kagan et al.
2005/0203344 A1 9/2005 Orban, III et al.
2005/0203550 A1 9/2005 Laufer et al.
2005/0216078 A1 9/2005 Starksen et al.
2005/0267405 A1 12/2005 Shah
2005/0273138 A1 12/2005 Starksen et al.
2006/0025750 A1 2/2006 Starksen et al.
2006/0025784 A1 2/2006 Starksen et al.
2006/0025789 A1 2/2006 Laufer et al.
2006/0025819 A1 2/2006 Nobis et al.
2006/0030884 A1 2/2006 Yeung et al.

(56) References Cited

U.S. PATENT DOCUMENTS

| | | | |
|---|---|---|---|
| 2006/0058817 | A1 | 3/2006 | Starksen et al. |
| 2006/0089646 | A1 | 4/2006 | Bonutti |
| 2006/0167477 | A1 | 7/2006 | Arcia et al. |
| 2006/0265042 | A1 | 11/2006 | Catanese, III et al. |
| 2006/0282081 | A1 | 12/2006 | Fanton et al. |
| 2007/0049929 | A1 | 3/2007 | Catanese, III |
| 2007/0049970 | A1 | 3/2007 | Belef et al. |
| 2007/0060931 | A1 | 3/2007 | Hamilton et al. |
| 2007/0088362 | A1 | 4/2007 | Bonutti |
| 2007/0112385 | A1 | 5/2007 | Conlon |
| 2007/0142846 | A1 | 6/2007 | Catanese, III et al. |
| 2007/0173888 | A1 | 7/2007 | Gertner et al. |
| 2007/0260259 | A1 | 11/2007 | Fanton et al. |
| 2008/0009888 | A1 | 1/2008 | Ewers et al. |
| 2008/0021445 | A1 | 1/2008 | Elmouelhi et al. |
| 2008/0033488 | A1 | 2/2008 | Catanese, III et al. |
| 2008/0039894 | A1 | 2/2008 | Catanese, III et al. |
| 2008/0045978 | A1 | 2/2008 | Kuhns et al. |
| 2008/0058710 | A1 | 3/2008 | Wilk |
| 2008/0065120 | A1 | 3/2008 | Zannis et al. |
| 2008/0082113 | A1 | 4/2008 | Bishop et al. |
| 2008/0086172 | A1 | 4/2008 | Martin et al. |
| 2008/0091220 | A1 | 4/2008 | Chu |
| 2008/0091237 | A1 | 4/2008 | Schwartz et al. |
| 2008/0119874 | A1 | 5/2008 | Merves |
| 2008/0154378 | A1 | 6/2008 | Pelo |
| 2008/0195145 | A1 | 8/2008 | Bonutti et al. |
| 2008/0208220 | A1 | 8/2008 | Shiono et al. |
| 2009/0012537 | A1 | 1/2009 | Green |
| 2010/0010631 | A1 | 1/2010 | Otte et al. |
| 2010/0114162 | A1 | 5/2010 | Bojarski et al. |
| 2010/0286106 | A1 | 11/2010 | Gat et al. |
| 2010/0286679 | A1 | 11/2010 | Hoey et al. |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Accepted Jun. 7, 2006.

Richard Berges et al., "Alternative Minimalinvasive Therapien Beim Benignen Prostatasyndrom", medizin, Jg, 104 heft 37, Sep. 14, 2007.

Rudolf Hartung, et al., Instrumentelle Therapie der benegnen Prostatahyperplasie, Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 194(36): A2424-9.

R. Hubmann, Geschichte der transurethralen Prostataeingriffe, Geschichte der Medizin, Urologe [B} 2000 40: 152-160.

U. Jonas, et al. Benigne Prostatahyperplasie, Der Urologe 2006, [Sonderheft] 45: 134-144.

O.A. Bacharova, et al. "The Effect of *Rhodiolae rosea* Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 209; 16 (1): 19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstraction in Male", Pharma Medica vol. 8 No. 8, p. 35-39.

O. Reich, et al., "Benignes Prostatasyndrom (BPS)", er Urologe A Issue vol. 45, No. 6, Jun. 2006, p. 769-782.

Daito Takashi, "Low-Invasive Treatment for BPH", Medico vol. 34, No. 10 p. 366-369.

Trapeznikov et al., "New Technologies in the Treatment of Benign Prostatic Hyperplasia", Urologia Nefrol (Mosk) 1996, Jul.-Aug. (4): 41-47.

Koyanagi Tomohiko, et al., "Surgery View of 21st Century", Urological Surgery, vol. 84, No. 1 p. 47-53.

Borzhievski et al., "Tactics of the Surgical Treatment of Patients With Prostatic Adenoma and Acute Urinary Retention", Urologia Nefrol (Mosk). Jan.-Feb. 1987 (1): 39-43.

Yeung, Jeff, "Treating Urinary Stress Incontinence Without Incision with Endoscopic Suture Anchor & Approximating Device," Aleeva Medical, Inc., 2007.

* cited by examiner

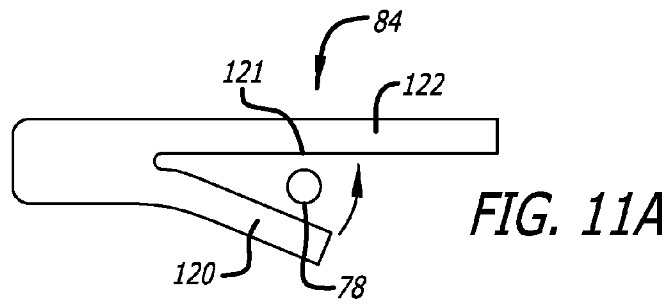
FIG. 11A
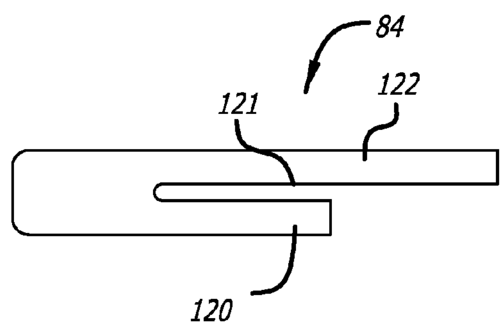
FIG. 11B
84
12D
130
132
12D
FIG. 12A
12E
84
130
12E
FIG. 12B
12F
84
130
12F
FIG. 12C
FIG. 12D
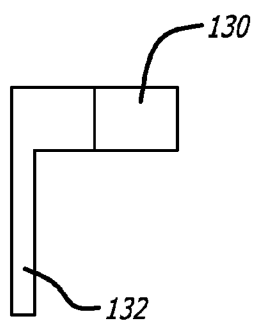
FIG. 12E
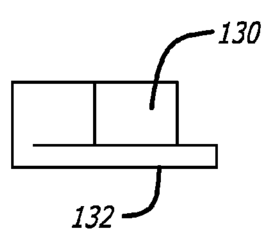
FIG. 12F
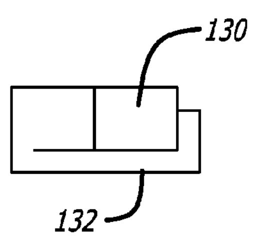

LATCHING ANCHOR DEVICE

CROSS-REFERENCE TO RELATED APPLICATIONS

This application is a continuation-in-part of: 1) copending U.S. patent application Ser. No. 12/852,243, filed Aug. 6, 2010; 2) copending U.S. patent application Ser. No. 12/512,674, filed Jul. 30, 2009 which claims the benefit of Provisional Application Ser. No. 61/084,937; 3) copending U.S. patent application Ser. No. 11/775,162, filed Jul. 9, 2007: 4) copending U.S. patent application Ser. No. 11/671,914, filed Feb. 6, 2007; 5) copending U.S. patent application Ser. No. 11/492,690, filed on Jul. 24, 2006; 6) copending U.S. patent application Ser. No. 11/833,660, filed on Aug. 3, 2007, which is a continuation of U.S. patent application Ser. No. 11/318,246, filed on Dec. 20, 2005; and 7) copending U.S. patent application Ser. No. 11/838,036 filed on Aug. 13, 2007, which is a continuation of U.S. patent application Ser. No. 11/134,870 filed on May 20, 2005; the entire disclosures of each of which are expressly incorporated herein by reference.

FIELD OF THE INVENTION

The disclosed embodiments relate generally to medical devices and methods, and more particularly to systems and associated methods for manipulating or retracting tissues and anatomical or other structures within the body of human or animal subjects for the purpose of treating diseases or disorders.

BACKGROUND

There are a wide variety of situations in which it is desirable to lift, compress or otherwise reposition normal or aberrant tissues or anatomical structures (e.g., glands, organs, ligaments, tendons, muscles, tumors, cysts, fat pads, and the like) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, and the like) and/or for cosmetic purposes (e.g., face lifts, breast lifts, brow lifts, and the like) and/or for research and development purposes (e.g., to create animal models that mimic various pathological conditions). In many of these procedures, surgical incisions are made in the body, and laborious surgical dissection is performed to access and expose the affected tissues or anatomical structures. Thereafter, in some cases, the affected tissues or anatomical structures are removed or excised. In other cases, various natural or man-made materials are used to lift, sling, reposition or compress the affected tissues.

Benign Prostatic Hyperplasia (BPH):

One example of a condition where it is desirable to lift, compress or otherwise remove a pathologically enlarged tissue is Benign Prostatic Hyperplasia (BPH). BPH is one of the most common medical conditions that affects men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH is expected to increase as the average age of the population increases in developed countries.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate, and the like.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine, and the like) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1 a-adrenergic receptors blockers and 5-alpha-reductase inhibitors. Alpha-1 a-adrenergic receptors blockers block the activity of alpha-1 a-adrenergic receptors that are responsible for causing constriction of smooth muscle cells in the prostate. Thus, blocking the activity of alpha-1 a-adrenergic receptors causes prostatic smooth muscle relaxation. This, in turn, reduces urethral resistance thereby reducing the severity of the symptoms. 5-alpha-reductase inhibitors block the conversion of testosterone to di-hydro-testosterone. Di-hydro-testosterone causes growth of epithelial cells in the prostate gland. Thus, 5-alpha-reductase inhibitors cause regression of epithelial cells in the prostate gland and, hence, reduce the volume of the prostate gland, which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus, the region of the urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases deep enough to cut the surrounding prostate gland tissue including the prostatic capsule. This releases any compression on the bladder neck and causes the bladder neck to spring apart. The incisions can be made using a resectoscope, laser beam, and the like.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium: Yttrium-aluminum-gamet (NdYAG) laser is used to ablate tissue by causing coagulation necrosis. The procedure is performed under visual guidance. In HoLEP, a holmium: Yttrium-aluminum-gamet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the lithium triborate (LBO) laser. The wavelength of this laser is highly absorbed by oxyhemoglobin. This laser vaporizes cellular water and, hence, is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland, thus, reducing the severity of BPH symptoms.

Another example of a minimally invasive procedure for treating BPH symptoms is Transurethral Needle Ablation (TUNA). In this procedure, heat-induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser-induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra, and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland, and laser energy is delivered through the distal tip for a desired time. This heats the middle lobe and causes laser-induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which, in turn, causes the prostate gland to shrink. Shrinkage of the prostate gland reduces the degree of squeezing of the urethra by the prostate, thus, reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1 a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only have a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra; need for a repeat surgery; and the like. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%). Typical recovery from TURP involves several days of inpatient hospital treatment with an indwelling urethral catheter, followed by several weeks in which obstructive symptoms are relieved, but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries has made their removal quite difficult and invasive.

Thus, the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and, in fact, often experiences worse symptoms for weeks after the procedure until the body begins to heal. Additionally, all device approaches require a urethral catheter placed in the bladder, and in some cases for weeks. In some cases, catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Cosmetic or Reconstructive Tissue Lifting and Repositioning:

Many cosmetic or reconstructive surgical procedures involve lifting, compressing or repositioning of natural tissue, natural tissue or artificial grafts, or aberrant tissue. For example, surgical procedures such as face lifts, brow lifts, neck lifts, tummy tucks, and the like, have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin, and then attaching the repositioned tissues to underlying or nearby structures (e.g., bone, periostium, or other muscles) to hold the repositioned tissues in their new (e.g., lifted) position. In some cases, excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted though relatively small incisions of puncture wounds.

There remains a need for the development of a suture lock or a suture anchor for use in various contemplated applications. In particular, there is a need for an anchor which can be easily configured to lockingly engage suture once access to an interventional site is achieved. The disclosed embodiments address these and other needs.

SUMMARY

Briefly and in general terms, the disclosed embodiments are directed towards an anchor assembly for use within a patient's body. In one embodiment, an anchor secures to a connector in the form of a suture. The structures can further form an assembly including a distal anchor connected to a proximal anchor.

In various approaches, the anchor can include a solid generally cylindrical or alternatively a tubular back end. The anchor can also include a pair of spaced apart prongs including a catch or latching structure extending therefrom. The spaced prongs join together at a slot inception. The prongs can include inwardly facing protrusions that are configured to capture and deform the suture between the protrusions and prevent the suture from disengaging from the anchor device once engaged. The mechanism of suture attachment and strength of the assembly is a combination of compression of the suture between the prongs of the anchor as well as disruption of the suture surface by the edges of the anchor. The edges provide a surface contact area between anchor prongs and focus the compressive forces that cause the suture to conform around both internal and external faces.

In one specific approach, one of the prongs of the anchor includes a mushroom head fastener which is lockingly received in a corresponding recess. In another approach, the prongs define locking scissors. In yet another approach, the prongs of the anchor include complementary structures including a slotted hole for locking the prongs together.

In other aspects, the anchor can include a first prong and a second prong having a greater length. A terminal end of the longer prong can be configured about the shorter prong to define grasping structure. Alternatively, the shorter prong can be placed into an interference engagement with the longer prong. In yet further aspects, the anchor can include a body with an extension which is capable of being folded laterally to engage a connector. The extension can be folded about the body and can be further engaged within a receiving substructure formed in the anchor body.

Other features and advantages will become apparent from the following detailed description, taken in conjunction with the accompanying drawings, which illustrate by way of example, the features of the various embodiments.

BRIEF DESCRIPTION OF THE DRAWINGS

FIGS. 11A-B are side views, depicting a latching anchor with interference structure;

FIGS. 12A-F are perspective and cross-sectional views, depicting yet a further approach to a latching anchor;

DETAILED DESCRIPTION

Figure 1:
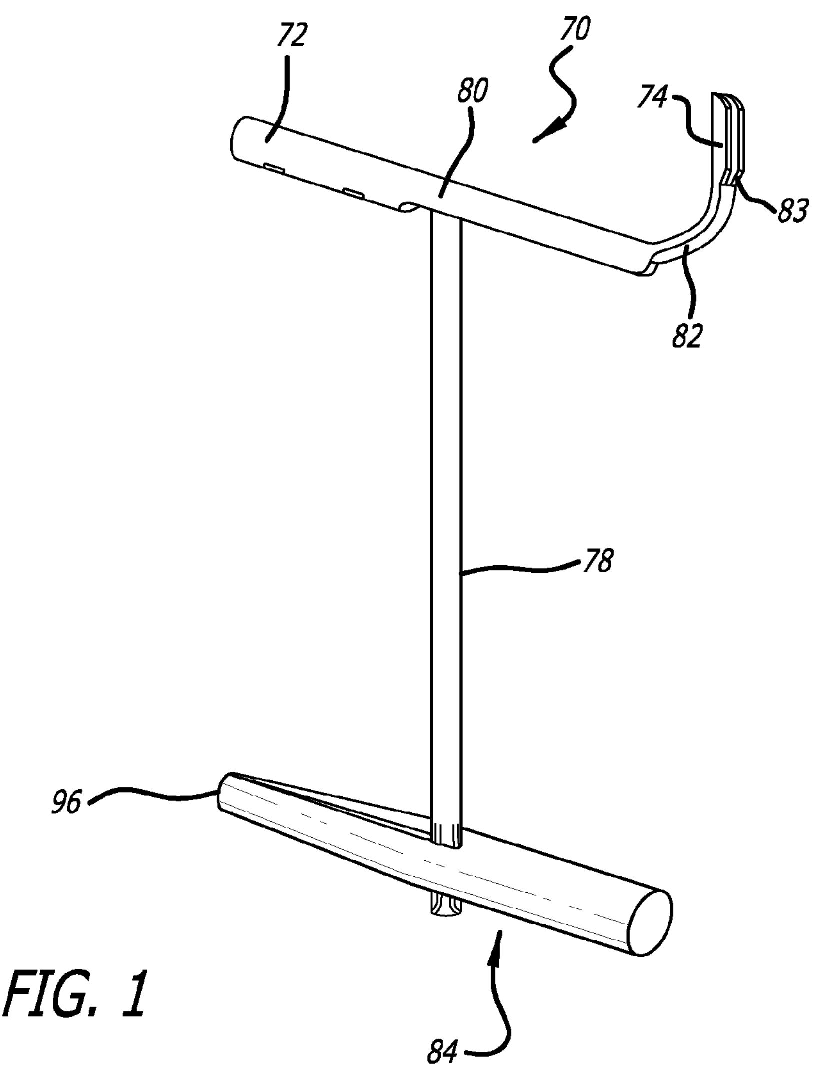
FIG. 1 is a perspective view of one embodiment of an anchor assembly that includes a distal anchor and a proximal anchor secured together by a suture.

Turning now to the figures, which are provided by way of example and not limitation, the disclosed embodiments are embodied in anchor assemblies configured to be delivered within a patient's body. As stated, the disclosed embodiments can be employed for various medical purposes including but not limited to retracting, lifting, compressing, supporting or repositioning tissues, organs, anatomical structures, grafts or other material found within a patient's body. Such tissue manipulation is intended to facilitate the treatment of diseases or disorders. Moreover, the disclosed embodiments have applications in cosmetic or reconstruction purposes, or in areas relating to the development or research of medical treatments. Referring now to the drawings, wherein like reference numerals denote like or corresponding components throughout the drawings and, more particularly to FIGS. 1-18, there are shown aspects of an anchor assembly.

In such applications, one portion of an anchor assembly is positioned and implanted against a first section of anatomy. A second portion of the anchor assembly is then positioned and implanted adjacent to a second section of anatomy for the purpose of retracting, lifting, compressing, supporting or repositioning the second section of anatomy with respect to the first section of anatomy, as well as for the purpose of retracting, lifting, compressing, supporting or repositioning the first section of anatomy with respect to the second section of anatomy. It is also to be recognized that both a first and second portion of the anchor assembly can be configured to accomplish the desired retracting, lifting, compressing, supporting or repositioning of anatomy due to tension supplied thereto via a connector assembly (e.g., suture) affixed to the first and second portions of the anchor assembly.

In one embodiment of the anchor assembly, the anchor assembly is configured to include structure that is capable of being implanted within a patient's body. The anchor assembly may also be used in conjunction with a conventional remote viewing device (e.g., an endoscope) so that an interventional site can be observed.

In one embodiment, the anchor assembly can be placed at an intervention site using a delivery tool. One specific, non-limiting application of the delivery tool is for the treatment of benign prostatic hyperplasia. In this procedure, an implant is delivered to a prostatic lobe that is obstructing the urethral opening and restricting flow. The implant compresses the lobe, thereby increasing the urethral opening and reducing the fluid obstruction through the prostatic urethra.

Additionally, in one embodiment, the anchor assembly is embodied in a tissue approximation anchor (TAA). The tissue approximation anchor is an implant assembly that includes one tubular member (preferably comprised of Nitinol or other comparable material), referred to as the capsular anchor or, more generally, distal anchor 70. The distal anchor 70 is preferably connected by a suture 78 to a slotted, flattened-tubular member (preferably comprised of stainless steel), referred to as the urethral anchor or proximal anchor 84. In one specific, non-limiting embodiment, the distal anchor 70 is comprised of an electro-polished Nitinol (nickel titanium alloy SE508, 55.8% nickel) tube.

The tissue approximation anchor is designed to be useable in an office environment (in contrast to requiring a hospital environment). The delivery tool is used through a 19Fr introducer sheath size in one preferred embodiment, while in another embodiment a sheath size of 21F is employed. Additionally, the material selection and construction of the tissue approximation anchor still allows for a subsequent TURP procedure to be performed, if necessary. In this suture-based, tissue approximation technique, a needle delivery mechanism is used to implant a nitinol distal anchor 70 and attached connector or suture 78. In one approach, the introducer sheath is first placed within a patient's urethra. An anchor housed within the delivery tool is then placed through the introducer sheath and a distal portion of the delivery tool is placed at the interventional site. Once the distal anchor 70 and attached suture 78 have been deployed, with the needle retracted and the suture 78 tensioned, the anchor 84 is pushed by the delivery tool and captures the suture 78 transverse to the anchor axis.

In one embodiment, the nitinol tube is attached to a USP size 0 PET (Poly Ethylene Terephthalate) monofilament suture 78 by thermally forming the suture to locking features on the distal anchor 70 (See FIG. 1). Referring again to the suture itself, the PET suture is a round monofilament extrusion/pulltrusion composed of a grade 8816 polyethylene terephthalate. Typically, the base material for the suture is annealed at approximately 191 degrees Celsius for approximately 5 minutes in a straight condition. In one non-limiting embodiment, the PET suture 78 has a diameter of 0.015 inches and a tensile strength greater than or equal to 6.0 pounds.

Figure 2:
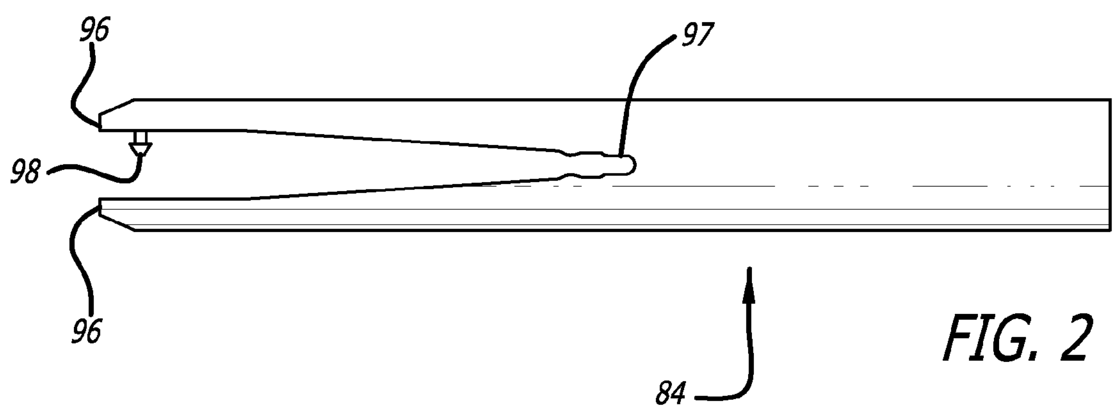
FIG. 2 is a top view of one embodiment of an anchor assembly.
Figure 3:
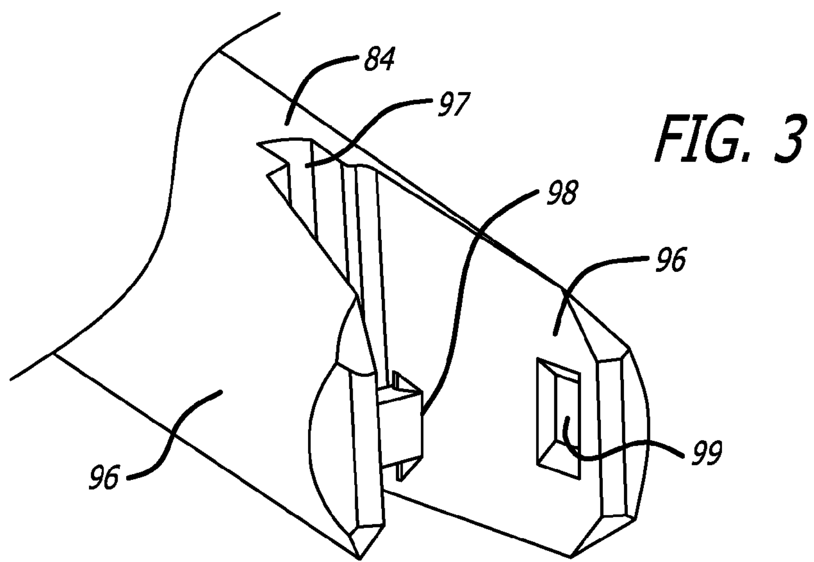
FIG. 3 is a close up perspective view of the latching structure of the anchor assembly of FIG. 2.

In one embodiment, as shown in FIGS. 2 and 3, the anchor 84 is a 316 L, stainless steel member that is slotted, electropolished, and passivated. The anchor 84 includes prongs 96 that can assume both open and closed positions and that grip and deform the suture 78 configured between the prongs 96. The interior structure of the prongs function to disrupt the surface of the suture 78, both biting into the suture 78 as well as compressing the suture 78 between the slotted prongs 96. A mushroom head tab 98 extends from one or more of the prongs 96, the tab 98 being configured to be lockingly received on a recess 99 formed in an opposing prong 96.

In one embodiment, the prongs 96 extend from a solid generally cylindrical structure. The wider and smoother prongs 96 of the anchor 84 assist in preventing the prongs 96 from irritating and/or damaging tissue, which is more likely to occur with a thinner and pointier leg structure.

In certain approaches, the slotted anchor 84 includes a rigid generally cylindrical back end 95, extending from which are a pair of spaced prongs 96. Terminal ends of the prongs 96 may be tapered to receive a section of the suture 78. Notably, the prong structure commences at a narrowed slot inception 97, which steps outwardly to a wider dimension to thereby define the space between the prongs 96. This narrow slot 97 provides the slotted anchor 84 with desired structure to receive the suture 78 and to facilitate locking engagement with the slotted anchor 84. Notably, in one embodiment the space between the prongs 96 of the slotted anchor 84 is dimensionally relative to the diameter of the suture 78 such that is has sufficient gripping force to obviate the need for a securing end unit. Accordingly, in a preferred embodiment, a securing end unit is not needed.

In one embodiment, shaped tube raw stock is used to produce the anchor 84 using slot/profile cutting. Specifically, in one embodiment the raw stock may be cut by laser, wire-EDM, or stamped from a flat and formed into a shape. In one non-limiting embodiment, the raw stock has a total height ranging from 0.020 inches to 0.025 inches, and has a total width ranging from 0.038 inches to 0.042 inches. Thus, this raw stock is flatter and wider than a purely round tube would be.

The inwardly facing structure of the prongs 96 of the anchor is configured to grasp and deform the suture 78. In one embodiment, the inner surface of the prongs 96 near the slot inception 97 is more of an extended landing than a simple U-shaped surface configuration. Thus, there is a longer dimension for better seating of the suture 78.

In one embodiment, a 0.014 inch gap between prongs 96 provides a structure suitable for tissue interaction and use with a 0.015 inch suture 78. It will be appreciated by those skilled in the art, that many variations in the slot parameters are possible for optimizing performance in different situations. Additionally, in some embodiments, the protrusions formed on opposite prongs may be of differing shapes. Such slot parameters include, by way of example only, and not by way of limitation: width, thickness, length, and profile. Optionally, the anchor assembly may be filled in with an RO material, or other therapeutic agent.

There can also be variations in the tab 98 and recess 99 configurations used to latch and lock the prongs 96 together as are approached to accomplish such locking. In contemplated approach for latching prongs 96 together, a delivery tool can include a sleeve (not shown) that is advanced over the prongs 96 to bring them into engagement, subsequent to positioning a connector between the prongs 96.

Figure 4:
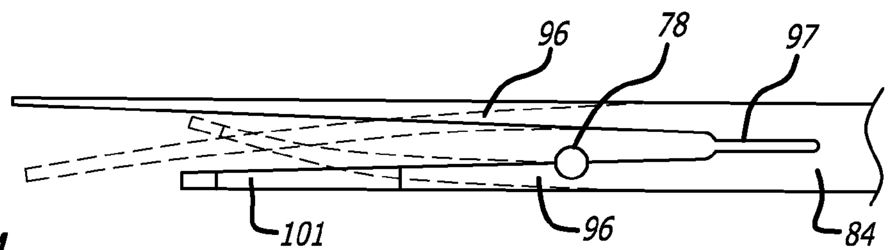
FIG. 4 is a side view of another embodiment of an anchor assembly.
Figure 5:
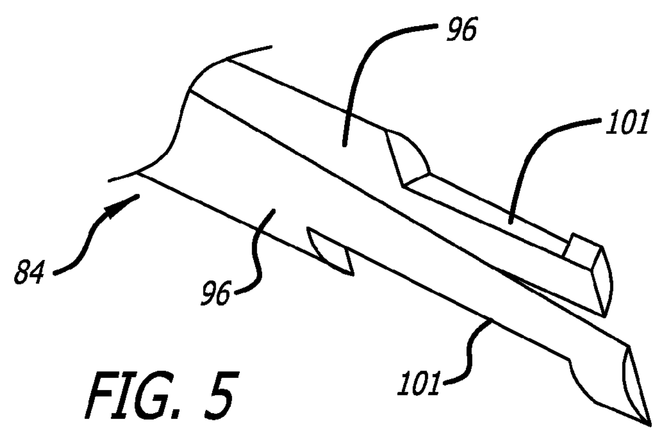
FIG. 5 is an end view of the anchor assembly of FIG. 4.

As shown in FIGS. 4 and 5, the anchor 84 can also include prongs 96 of different lengths configured to form a scissor-like arrangement. The prongs 96 can further include complementary cut-outs 101 which function to retain the prongs 96 in a closed, locking engagement after a connector 78 is placed as desired therebetween. Again, deflection of the prongs 96 into locking engagement can be accomplished in various conventional approaches, such as including structure that transmits a force in a lateral direction.

Figure 6:
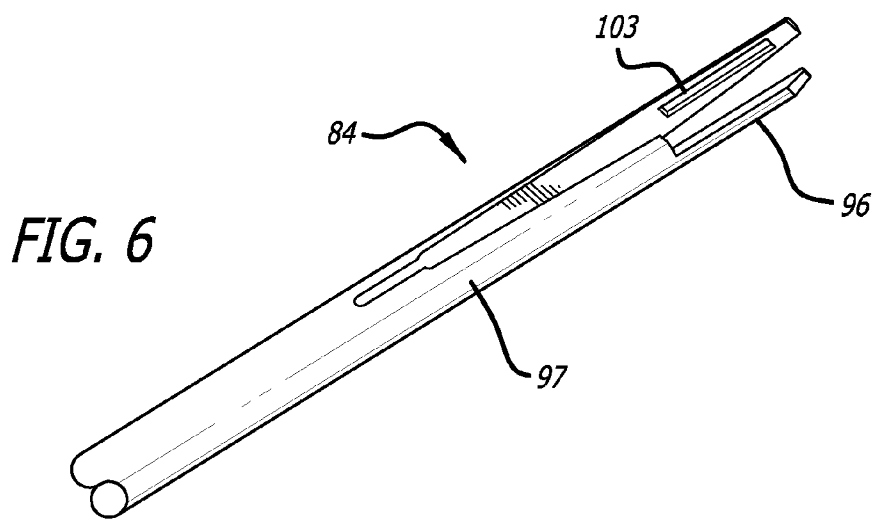
FIG. 6 is a perspective view of another approach to an anchor assembly.
Figure 7:
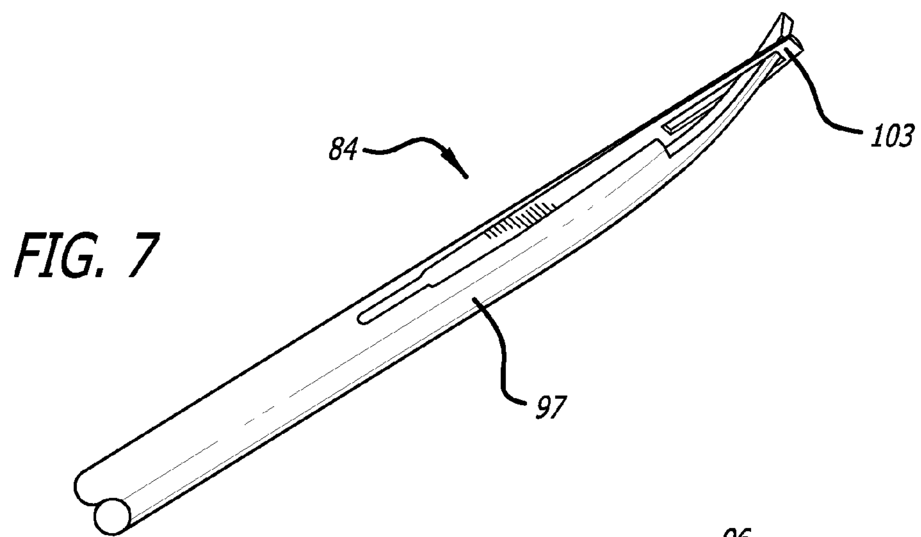
FIG. 7 is a perspective view, depicting a deformed configuration of the anchor of FIG. 6.
Figure 8:
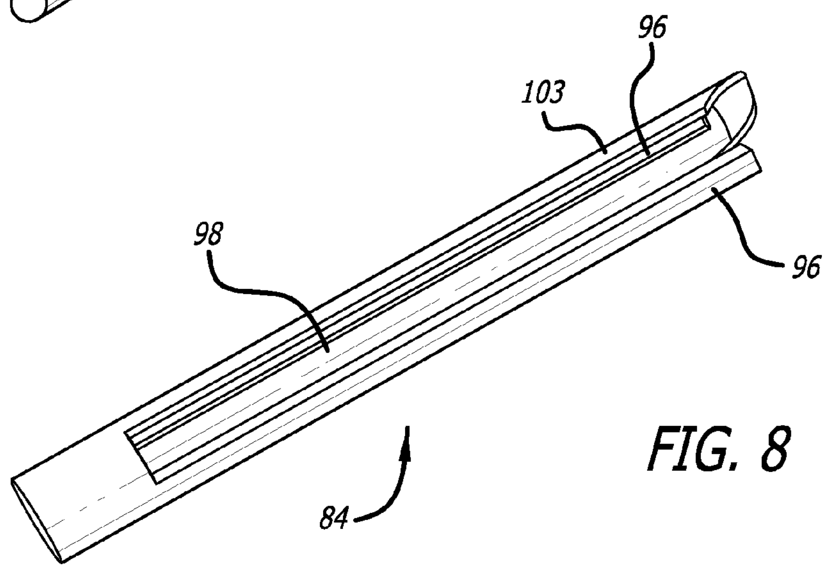
FIG. 8 is a perspective view, depicting latching anchor formed from a tube.
Figure 9A:
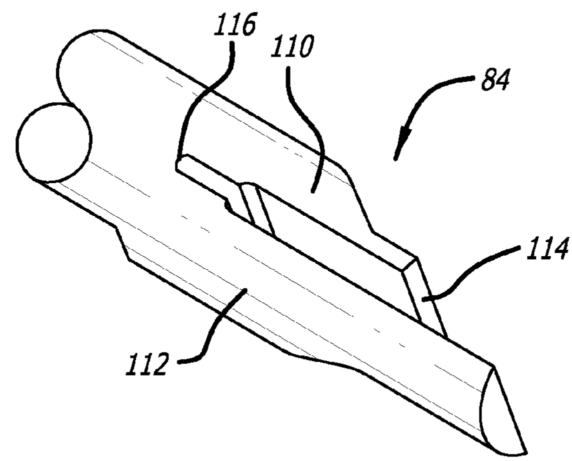
FIGS. 9A-B are perspective views, depicting another approach to a latching anchor.
Figure 9B:
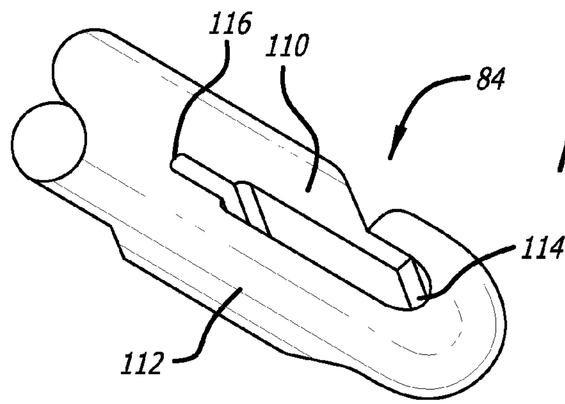

Turning now to FIGS. 6 and 7, yet another approach to a latching anchor 84 is shown. Here, one prong 96 includes a slot 103 formed near a distal end thereof and which is sized and shaped to lockingly latch another prong 96. In still yet another contemplated design (See FIG. 8), the anchor 84 is formed of tubular structure. One prong lockingly engages a curved interior surface 98 of a second prong.

Figure 10A:
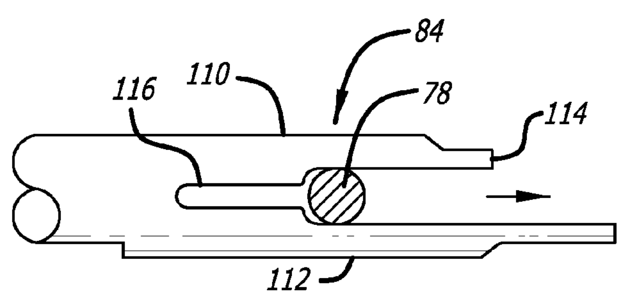
FIGS. 10A-B are side views, depicting yet a further approach to a latching anchor.
Figure 10B:
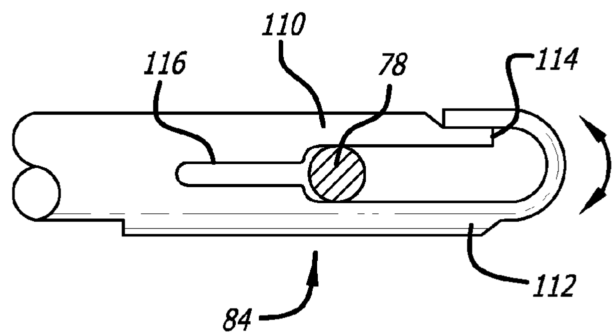
Figure 13A:
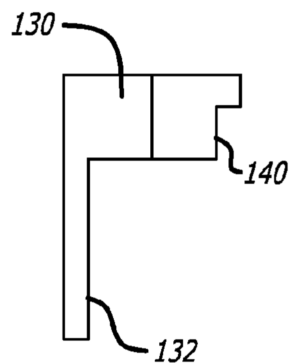
FIGS. 13A-15B are cross-sectional views, depicting alternative embodiments of the anchor approach depicted in FIGS. 12A-C.
Figure 13B:
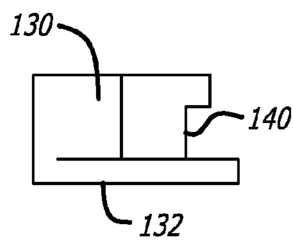
Figure 13C:
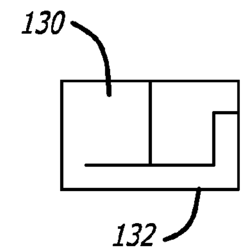
Figure 14A:
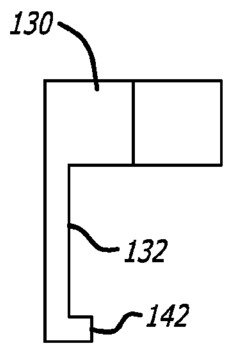
Figure 14B:
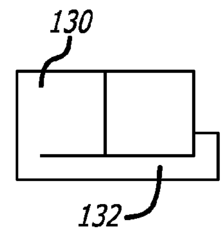

As shown in FIGS. 9A-B and FIGS. 10A-B, further approaches to a proximal anchor 84 can be embodied in a structure including prongs 110, 112 having different lengths. The longer prong 112 is designed to be folded laterally over a terminal end 114 of the shorter prong 110 to define a latching assembly substructure. In one approach, the lateral fold can be pre-formed into the anchor 84. Alternatively, the lateral fold can be formed in situ by advancing the anchor 84 against a curved wall or closed recess. Moreover, the slot 116 existing between the prongs 110, 112 can be formed by two generally parallel walls such as that shown in FIGS. 9A-B or alternatively, the slot 116 can be stepped as depicted in FIGS. 10A-B. In one aspect, the stepped slot is contemplated to facilitate a robust engagement with a suture or connector 78 by providing desired deformation of the connector 78.

In a related approach (FIGS. 11A-B), a proximal anchor 84 can include prongs configured to define an interference connection therebetween. Rather than laterally folding a longer prong over a terminal end of a shorter prong, however, this approach involves translating a shorter prong 120 into an interference recess 121 formed in a longer prong 122. Once the shorter prong 120 is placed into an interfering relationship with the longer prong 122, a connector 78 placed between the prongs 120, 122 can be fixedly engaged.

Figure 15A:
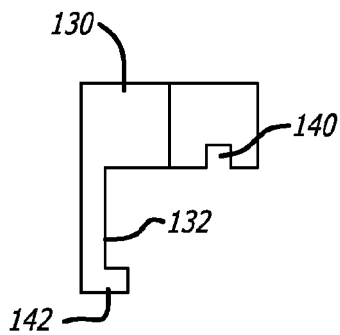
Figure 15B:
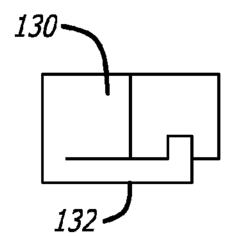

Various additional and related approaches to a latching proximal anchor with a pair of prongs are shown in FIGS. 12A-F, 13A-C, 14A-B and 15A-B. As shown in FIGS. 12A-C, the proximal anchor 84 can include a body 130 with an extension 132 projecting perpendicularly therefrom. The extension 132 is folded transverse to a long dimension of the body 130 to capture a connector (not shown). In a first approach (FIGS. 12D-F), the extension 132 is across a width of the body 130 and latched on an opposite side of the body 130. In alternate approaches, the body can include a recess 140 (FIGS. 13A-C and 15A-B) into which the extension 130 can be received. Additionally, the extension 130 can include a pre-formed angled terminal end 142 received on an opposite of the body 130 from which the extension projects (FIGS. 14A-B) or within the recess 140 (FIGS. 15A and B). In each of these approaches, the extension 130 and body 132 cooperate to fixedly grasp the connector.

Figure 16:
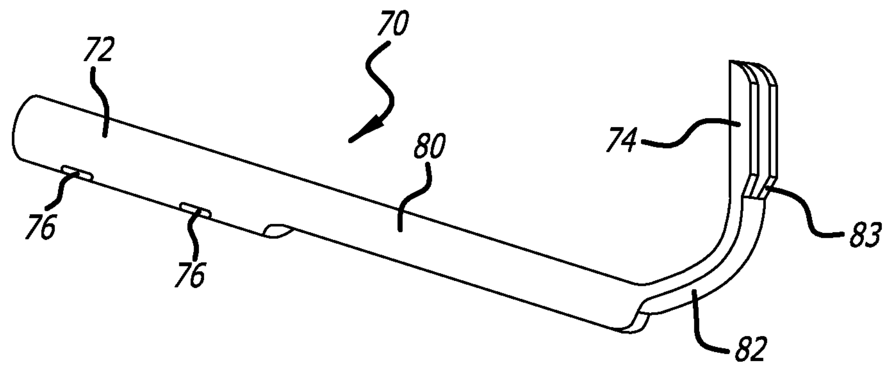
FIG. 16 is a perspective view of the distal anchor with a orthogonally oriented tail portion.
Figure 17:
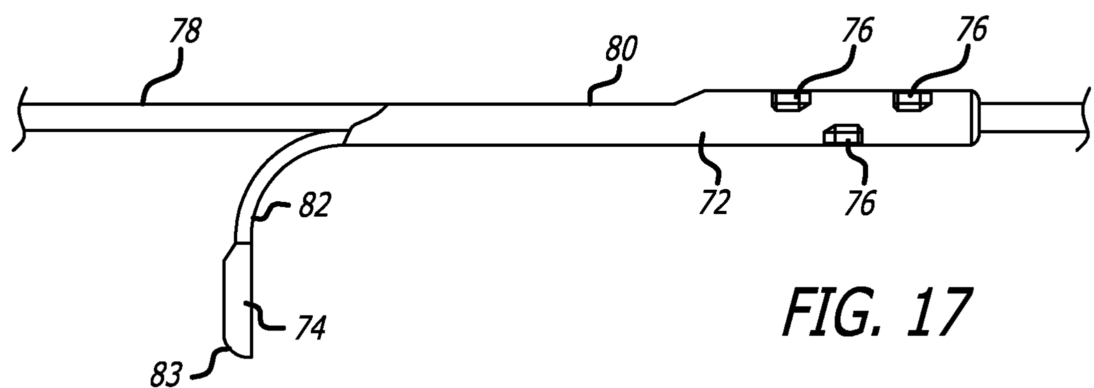
FIG. 17 is a side view of the distal anchor with a orthogonally oriented tail portion of FIG. 16 and the suture.

One embodiment of a distal anchor assembly 70 is depicted in FIGS. 16 and 17. In its unconstrained configuration, the distal (e.g., capsular) anchor 70 includes a tubular (head) portion 72 which is generally orthogonally oriented to a tail portion 74. It is to be noted, however, that while housed in a delivery assembly and prior to deployment at a target area, the distal anchor 70 is constrained to define a generally straight configuration, only subsequently assuming the unconstrained (i.e., orthogonally oriented) configuration upon deployment from a delivery device.

The distal anchor 70 is laser cut or wire EDM (electrical discharge machined) from a nitinol base stock that is generally-tubular is shape. The Nitinol distal anchor is shape-set to have a "flipping tail" and is electro-polished. The suture 78 is then attached to the distal anchor 70 as an adhesive free joint. Specifically, in one embodiment, the PET suture 78 is thermoformed onto locking features in the anchor 70. The distal anchor 70 may be locally heated to re-flow the suture onto the end of the anchor 70 and into cutouts on the anchor 70. Continuing, in one non-limiting embodiment, the post electro-polished distal anchor 70 has a 0.016 inner diameter and a 0.0253 outer diameter.

In one non-limiting embodiment, the tubular portion 72 of the distal anchor 70 includes a plurality of tabs 76 which can be deformed or deflected to accomplish affixing the distal anchor 70 to a suture 78. It has been found that three such tabs 76, two on one side of the tubular portion 72 and one on an opposite side, provide a sufficient connecting force and a desired balance between the suture 78 and distal anchor 70 and to move the distal anchor 70 by applying a force either in the proximal or distal direction. However, the distal anchor 70 may be attached to the suture 78 through any of several known techniques, such as by being attached to the distal end of the tubular portion 72.

In another aspect of a non-limiting embodiment, it is contemplated that the distal anchor 70 can be laser cut from a tube formed of Nitinol or other appropriate material. A mid-section 80 of the distal anchor 70 provides a structural transition from the tubular portion 72 to the tail portion 74. As such, a portion of a side wall is removed in the mid-section area 80. A further portion of the side wall is removed to define a connector section 82 of the tail 74 which extends from the mid-section 80. In one embodiment, this connector section 82 includes a bend that creates the orthogonally oriented configuration. This connector section 82 acts as a barb or deflected strut to cause flipping (creating a "flipping tail") and produce the relative unconstrained (orthogonally oriented) angle assumed between the tail 74 and tubular portion 72 of the distal anchor 70. The recovered shape of the terminal end portion 83 of the anchor presents a transverse strut that engages tissue when the suture is tensioned.

Thus, in its pre-implanted form, the anchor assembly can include a distal anchor 70 (e.g., first anchor) whose initial engagement with a suture 78 is generally coaxial, and a proximal anchor 84 (e.g., second anchor) with an initial engagement being generally perpendicular with the suture 78.

As stated above, an introducer sheath (not shown) can first be placed within a patient's urethra for the purpose of facilitating access to a treatment site. The distal anchor 70 is "unsheathed" from the needle delivery mechanism once positioned for reliable deployment eliminating predicate distal suture. This results in an adjustable implant length. This distal anchor 70 configuration also provides increased yield and strength.

With reference now to FIGS. 18A-F, in one particular, non-limiting use in treating a prostate, an elongate tissue access portion 404 of a delivery device 400 is placed within a urethra (UT) leading to a urinary bladder (UB) of a patient. The delivery device can be placed within an introducer sheath previously positioned in the urethra or alternatively, the delivery device can be inserted directly within the urethra. The patient is positioned in lithotomy. The elongate portion 404 is advanced within the patient until a leading end 410 thereof reaches a prostate gland (PG). In a specific approach, the side(s) (i.e., lobe(s)) of the prostate to be treated is chosen while the device extends through the bladder and the device is turned accordingly. The device is first positioned at the bladder neck and then retracted approximately 1 cm while keeping the device parallel to the prostatic fossa and preserving mucosa. The distal end of the elongate portion can be used to push the urethra into the prostate gland. The inside of the prostate gland (i.e., adenoma) is spongy and compressible and the outer surface (i.e., capsule) of the prostate gland is firm. By the physician viewing with the endoscope, he/she can push the urethra into the prostate gland compressing the adenoma and creating the desired opening through the urethra. To accomplish this, the physician pivots the tool laterally about the pubic symphysis, generally about 20 to 30 degrees (See FIG. 18A). The physician then rotates the tool anterior between 9 and 10 o'clock for the patient's side right lobe and between 2 and 3 o'clock for the patient's side left lobe. Viewing through the endoscope, the physician wants to have about the same amount of tissue protruding on both sides of the elongate shaft (See FIG. 18B).

Figure 18A:
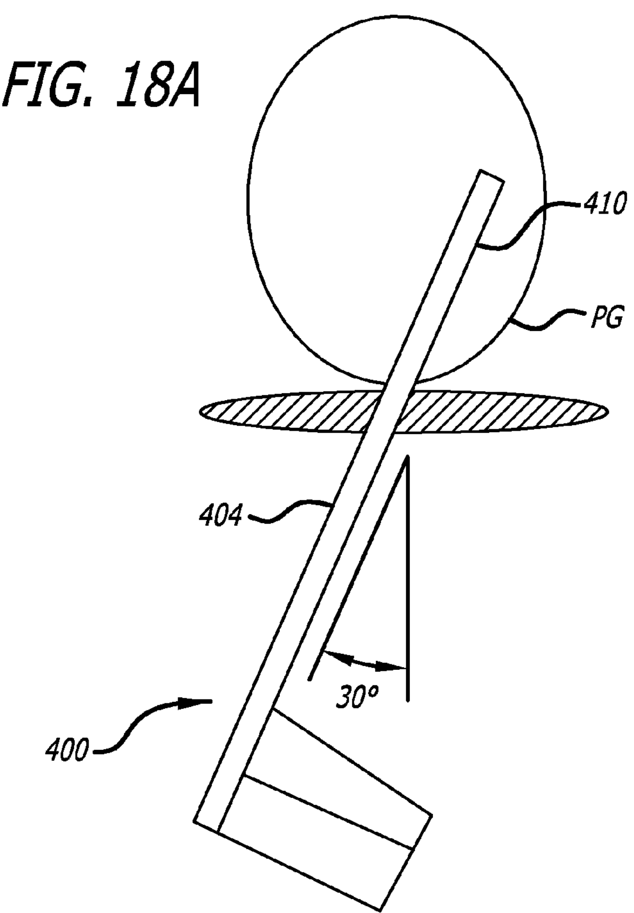
FIGS. 18A-F are partial cross sectional views of an anchor assembly of FIG. 1 being implanted through the prostate of an individual with Benign Prostatic Hyperplasia.
Figure 18B:
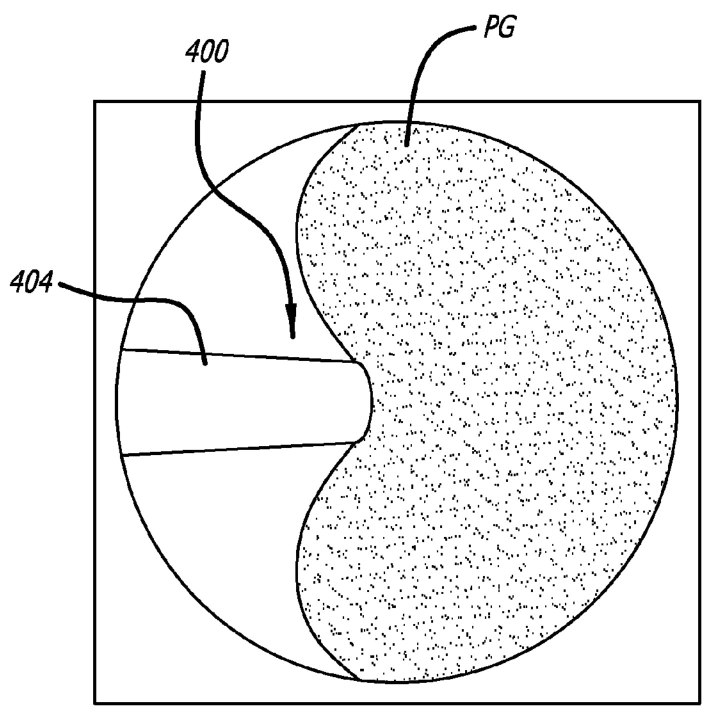
Figure 18C:
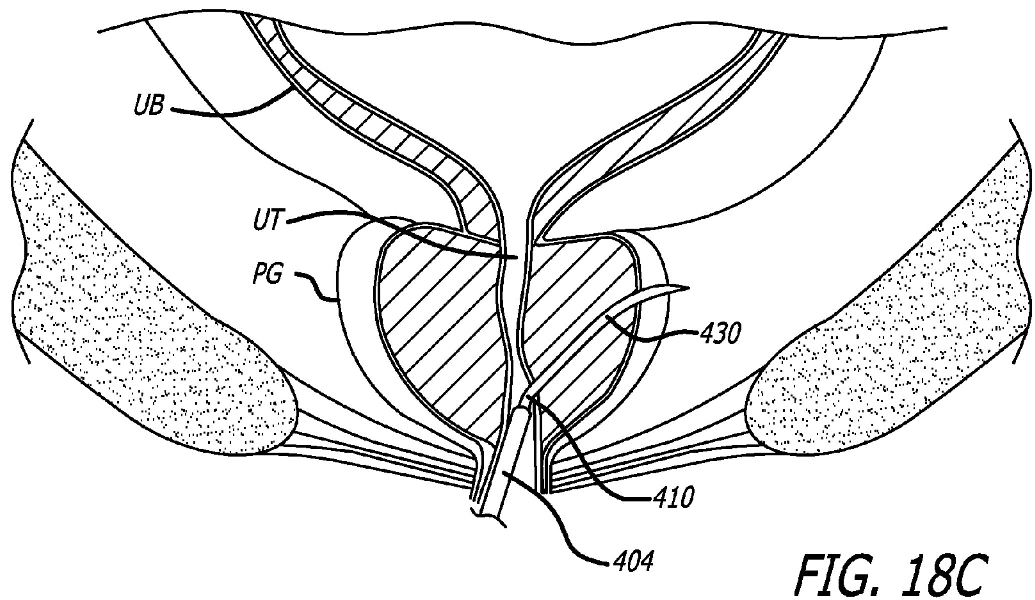
Figure 18D:
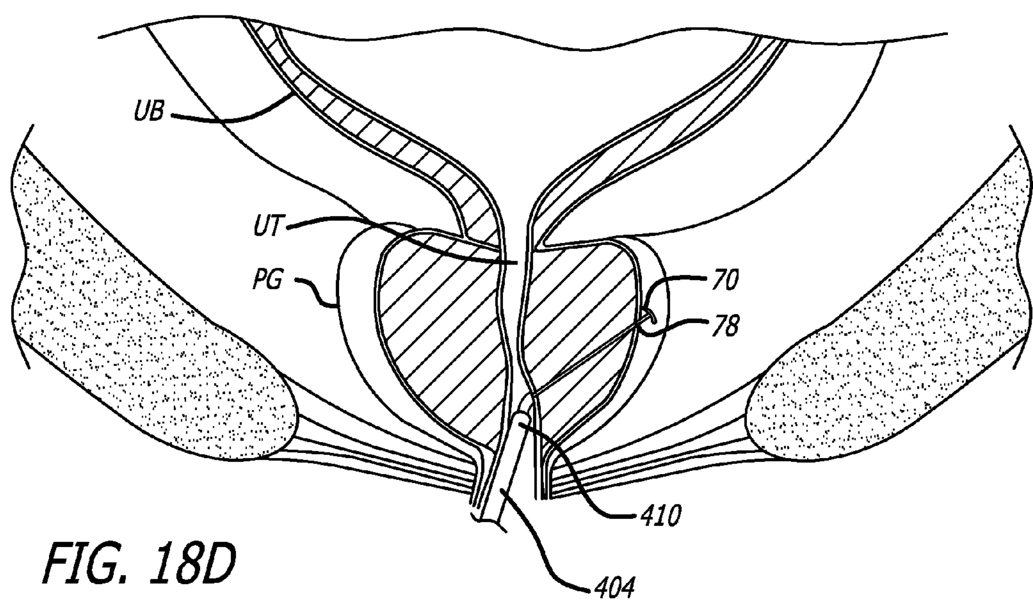

At the leading end 410 of the delivery device, as shown in FIG. 18C, a needle 430 carrying an anchor assembly is ejected into and through tissue. The needle assembly can be configured so that it curves back toward the delivery tool as it is ejected. In use in a prostate intervention, the needle assembly 430 is advanced through and beyond a prostate gland (PG). The delivery device can be rotated anteriorly to lift a prostatic lobe.

Figure 18E:
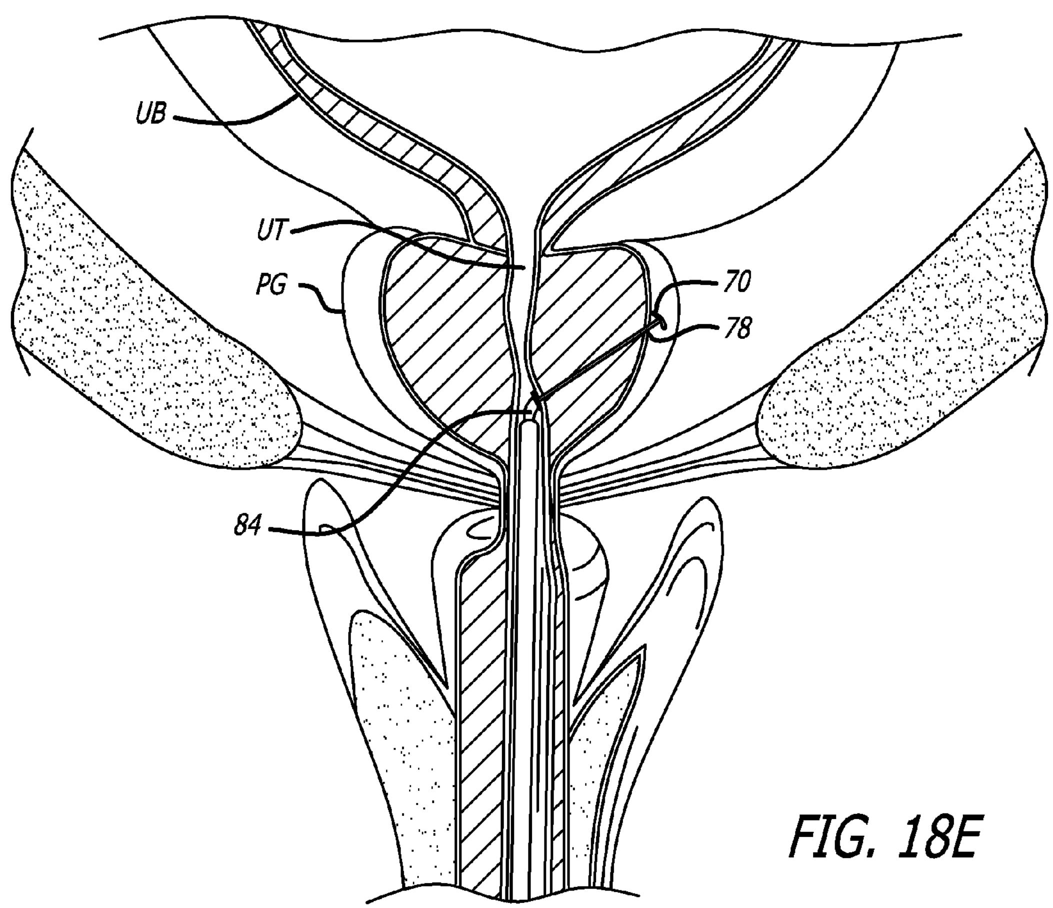

Upon withdrawal of the needle assembly 430 (See FIG. 18D), the distal anchor 20 is left beyond the prostate (PG). Next, steps are taken to implant the proximal anchor 84 within the urethra (FIG. 18E). Either a single anchor assembly or multiple anchor assemblies can be delivered and deployed at an intervention site by the deployment device (See FIG. 18F). Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

The disclosed embodiments contemplate both pushing directly on anchor portions of an anchor assembly as well as pushing directly upon the connector of the anchor assembly. Further, an anchor assembly can be delivered and deployed at an interventional site by a deployment device. Consequently, in the context of prostate treatment, the disclosed embodiments accomplish both compressing of the prostate gland and the opening of the prostatic urethra and applying tension between ends of the implant. Moreover, drug delivery is contemplated as a further remedy in BPH and over-active bladder treatment.

Once implanted, the anchor assembly of the disclosed embodiments accomplishes desired tissue approximation, manipulation, compression or retraction, as well as cooperates with the target anatomy to provide an atraumatic support structure. In particular, the shape and contour of the anchor assembly can be configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly, and new cell growth occurs over time. Such cooperation with target tissue facilitates healing and avoids unwanted side effects such as calcification or infection at the interventional site.

Furthermore, in addition to an intention to cooperate with natural tissue anatomy, the disclosed embodiments also contemplate approaches to accelerate healing or induce scarring. Manners in which healing can be promoted can include employing abrasive materials, textured connectors, biologics and drugs.

Figure 18F:
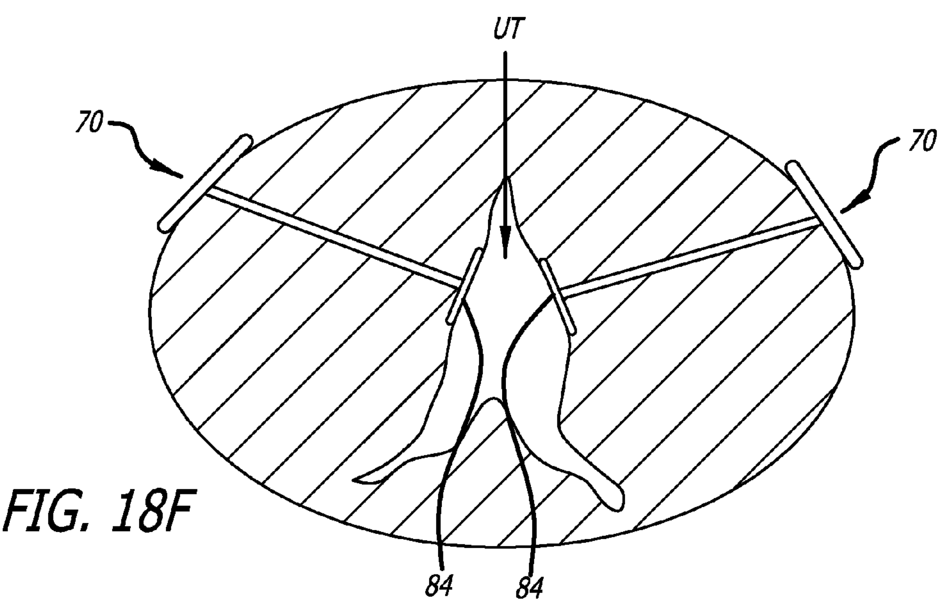

It has been observed that placing the anchors at various desired positions within the anatomy can extract the best results. For example, when treating a prostate, one portion of an anchor can be placed within a urethra. It has been found that configuring such anchors so that ten o'clock and two o'clock positions (when looking along the axis of the urethra) are supported or retained, effectively holds the anatomy open and also can facilitate invagination of the anchor portion within natural tissue. Typically, one to two pairs of anchor assemblies are implanted to create an anterior channel along the urethra within the prostate gland (FIG. 18F). This is particularly true in the regions of anatomy near the bladder and the juncture at which the ejaculatory duct connects to the urethra.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra. It is to be recognized that various materials are contemplated for manufacturing the disclosed devices. Moreover, one or more components such as distal anchor 70, proximal anchor 84, suture 78, of the one or more anchor assemblies disclosed herein may be designed to be completely or partially biodegradable or bio-fragmentable.

Further, as stated, the systems and methods disclosed herein may be used to treat a variety of pathologies in a variety of tubular structures comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, and the like.

Finally, it is to be appreciated that the invention has been described hereabove with reference to certain examples or embodiments, but that various additions, deletions, alterations and modifications may be made to those examples and embodiments without departing from the intended spirit and scope of the disclosed embodiments. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

The various embodiments described above are provided by way of illustration only and should not be construed to limit the disclosed embodiments. Those skilled in the art will readily recognize various modifications and changes that may be made to the disclosed embodiments without following the example embodiments and applications illustrated and described herein, and without departing from the true spirit and scope of the disclosed embodiments, which is set forth in the following claims.

What is claimed:

1. An anchor assembly, comprising:

a distal anchor, a connector and a proximal anchor, wherein the distal anchor is attached to an end portion of the connector, the proximal anchor comprising: a back end; and a pair of spaced prongs extending from the back end, the prongs being joined together at a slot inception, and wherein the prongs are shaped and sized of a configuration to provide deflection of the prongs;

wherein the prongs include inwardly facing structure configured to capture the connector therebetween and a latching structure configured to maintain an engagement with the connector between the prongs;

wherein the latching structure includes a frictionally engaging tab formed on one prong and a complementary recess formed in another prong;

wherein the proximal anchor is defined by a tubular member oriented along a longitudinal axis of the proximal anchor.

2. The anchor assembly of claim 1, wherein the prongs can assume an open position and a closed position and deform the connector in the closed position.

3. The anchor assembly of claim 1, wherein the latching structure defines a mushroom shaped tab.

4. The anchor assembly of claim 1, the proximal anchor including a first prong and a second prong, the second prong having a greater length than the first prong.

5. The anchor assembly of claim 4, the proximal anchor further comprising a slot inception, the slot inception is stepped and sized to accept and deform the connector.

6. The anchor assembly of claim 1, the distal anchor comprising a laterally oriented tail.

7. The anchor assembly of claim 6, the distal anchor further comprising a tubular portion which is generally perpendicular to a tail portion.

8. The anchor assembly of claim 7, wherein the tubular portion includes affixing tabs for affixing the distal anchor to the connector.

* * * * *